United States Patent [19]
Berglund et al.

[11] Patent Number: 6,116,097
[45] Date of Patent: Sep. 12, 2000

[54] METHOD AND MEANS FOR DETECTING CHEMICALS ON GROUND

[76] Inventors: Tage Berglund, Postlåda 29, SE-911 92 Vännäs; Sune Nyholm, Gimoborgsvagen 12, SE-907 42 Umeå; Göran Olofsson, Björnvägen 332A, SE-902 43, Umeå, all of Sweden

[21] Appl. No.: 09/355,964
[22] PCT Filed: Feb. 20, 1998
[86] PCT No.: PCT/SE98/00300
§ 371 Date: Aug. 19, 1999
§ 102(e) Date: Aug. 19, 1999
[87] PCT Pub. No.: WO98/37398
PCT Pub. Date: Aug. 27, 1998

[30] Foreign Application Priority Data

Feb. 21, 1997 [SE] Sweden .................................. 9700621

[51] Int. Cl.[7] .................................................... G01N 1/00
[52] U.S. Cl. ............................................................ 73/863.12
[58] Field of Search ................................ 73/863, 863.11, 73/863.12, 863.21–863.24, 863.33, 864.31, 864.33, 864.34, 864.51, 864.71, 864.73, 864.81, 31.02, 31.01, 23.31, 865.8

[56] References Cited

U.S. PATENT DOCUMENTS

| | | | |
|---|---|---|---|
| 3,420,091 | 1/1969 | Franklin | 73/863.33 |
| 3,793,887 | 2/1974 | Anderson et al. | 73/863.11 |
| 4,738,147 | 4/1988 | Tomlin | 73/863.11 |
| 4,982,616 | 1/1991 | Koch et al. | 73/864.81 |
| 5,437,203 | 8/1995 | Koch et al. | 73/864.71 |
| 5,517,026 | 5/1996 | Sickenberger et al. | 250/288 |

FOREIGN PATENT DOCUMENTS

| | | |
|---|---|---|
| 0 364 687 | 4/1990 | European Pat. Off. . |
| 2 259 572 | 3/1993 | United Kingdom . |
| 2 272 518 | 5/1994 | United Kingdom . |

*Primary Examiner*—Robert Raevis
*Attorney, Agent, or Firm*—Jacobson, Price, Holman & Stern, PLLC

[57] ABSTRACT

The invention relates to a method and means for detecting chemical contaminants on the ground. A tracked or wheeled vehicle is driven on the ground in question and a sampling screen (2) arranged as a mudflap in connection with at least one track/wheel of the vehicle is thereby contaminated by particles (3) thrown up from the ground, and an air stream carrying substances evaporated from said particles is caused to flow from said sampling screen (2) through a conduit (6) via a detection unit (4) in the vehicle. The sampling screen (2) is preferably provided with a heating device (11) to enhance the evaporation of possible chemicals from said particles.

12 Claims, 1 Drawing Sheet

METHOD AND MEANS FOR DETECTING CHEMICALS ON GROUND

The invention relates to a method and means for detecting chemical contaminants on the ground. More specifically, the invention relates to a method and means for carrying out the detection from a moving vehicle.

At chemical and nuclear energy accidents such as release of toxic and hazardous compounds and at radioactive fallout and chemical attack during war, safe and rapid detection and mapping is essential for the continued work. Vehicles equipped with personal protection for the crew, so that the vehicles can be used in areas contaminated with chemical warfare agents or radioactive fallout, are previous known. Equipment for mapping radioactive fallout situations are relatively well provided for, but the presence of chemicals of low volatility on the ground can be difficult to detect. Chemical warfare agents are dispersed as droplets and can at low temperatures remain as a ground contamination for a considerable time and involve a urgent danger—contact risk—even if the evaporation and consequently the concentration in the surrounding air is low. The equipment used today for vehicle based mobile detection of chemical warfare agents present as a ground contamination is based on the principle that a sample is first taken from the ground surface, i.e. with a special silicon wheel which after sampling is lifted and analysed (Fuchs), or by measuring compounds in the form of vapour in the ambient air on different heights over the ground surface. The British Patent 2 259 572 relates to an equipment of the latter type.

An object of the present invention is to provide a simplified method and simplified means for vehicle based mobile detection of chemical contaminants on the ground and to make it possible to detect also small amounts of compounds with extremely low volatility and under difficult conditions such as low temperatures.

The invention is based on the recognition that when a vehicle is driven through a chemically contaminated area, for instance on a road or in the terrain, the vehicle will become more or less spattered, contaminated, by the chemical in question. All transport from the contaminated ground to the vehicle is caused by the wheels or tracks contacting the ground. The spattering is mainly directed backwards towards the area where cars usually have mudflaps. According to the invention, this fact has been utilised to achieve a method and means for detecting chemical contaminants on the ground.

The inventive method is characterised in that a wheeled or tracked vehicle having a sampling screen arranged as a mudflap in connection with at least one wheel/track of the vehicle is driven on the ground to be investigated, whereby said sampling screen is contaminated by particles thrown up from the ground, and that an air stream carrying substances evaporated from said particles is caused to flow from said sampling screen through a conduit via a detection unit in the vehicle.

In order to increase the evaporation of substances from the particles, the sampling screen preferably has a heating device.

The air stream carrying evaporated substances to the detection unit can be a result of the speed of the vehicle or be accomplished by a fan/air pump in the conduit.

At dry conditions a sprinkling device can be used for wetting the wheel with a liquid to increase the spatter of particles and consequently the sensitivity of the detection.

The vehicle can be a car, all terrain carrier, armoured personnel carrier etc. but can also be a trailer, which is equipped for the purpose. The track/wheel of the vehicle that is used for spattering particles on to the sampling screen does not have to be one of the regular tracks/wheels of the vehicle but can constitute a separate unit. When detecting CW agents or similar toxic compounds the vehicle can be equipped with a so called collective protection for the crew. That is, the vehicle is tight, an overpressure can be maintained in the passenger compartment and incoming ventilating air is filtered through a chemical agent adsorbing filter.

By the inventive method very small amounts of ground contaminating chemicals can quickly be detected while the vehicle is cruising over the area. Because of the heating of the sampling screen, also extremely persistent compounds can be detected and the detection can be made in winter time at low temperatures.

The invention also relates to means for carrying out the method.

The invention will now be described in more detail with reference to the accompanying drawings.

The corresponding details in the two figures have been given the same reference numerals.

Figure 1:
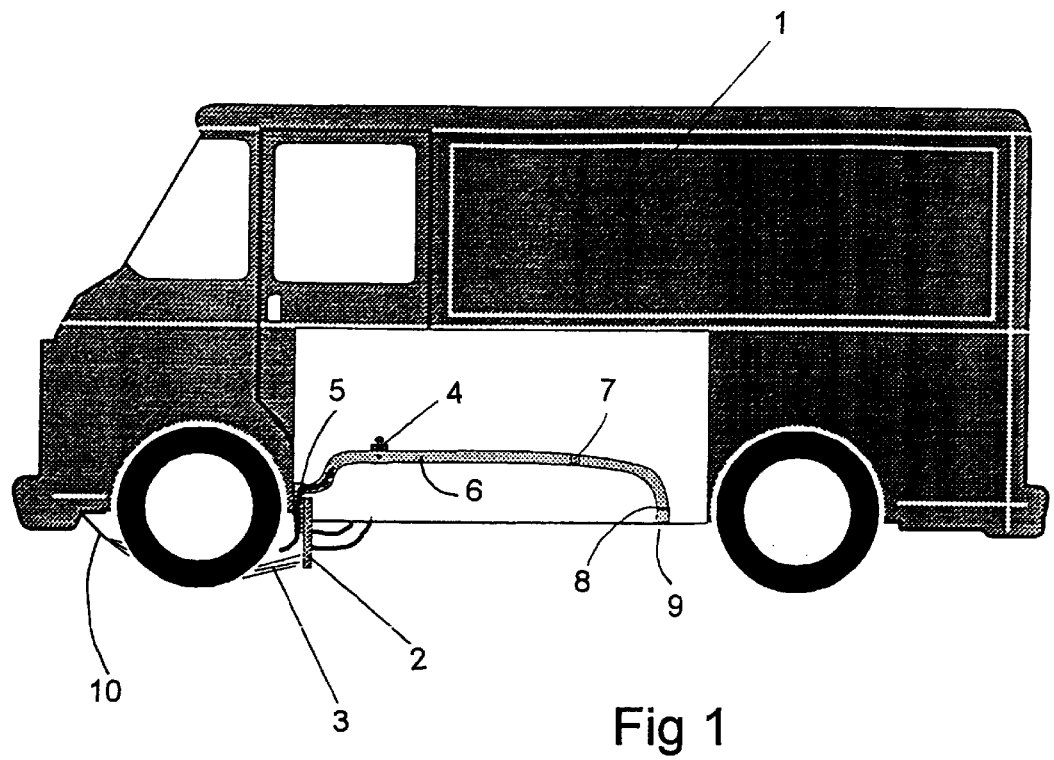
FIG. 1 is a side view of a wheeled vehicle according to the invention. A cut open section shows hidden details for conducting an air stream via a detection unit.

FIG. 1 shows an embodiment of a wheeled vehicle 1 equipped for detection of chemical contaminants on the ground. A sampling screen 2 is arranged as a mudflap at one of the front wheels of the vehicle. The screen is contaminated by particles thrown up from the ground when the vehicle passes an area to be investigated. Means being arranged for conducting an air stream from the sampling screen 2 via a detection unit 4 in the vehicle. In the embodiment shown said means consists of an air intake 5, a conduit 6 and a fan or an air pump 7. The conduit 6 leads the air stream from the air intake 5, into the vehicle via the detection unit 4 and ends in an air outlet 9 on the outside of the vehicle. The fan/air pump 7 is arranged in the conduit 6 to increase the flow rate. The air stream can also be accomplished by the pressure of the wind against the sampling screen, but a flow rate independent of the movement of the vehicle is to be preferred. The fan/air pump is suitably mounted after the detection unit 4 in the conduit so that air is sucked from the intake via the detection unit. Further, a throttle-valve 8 is arranged in the conduit 6 and is used in combination with the fan/air pump to control the flow rate. In case of small amounts of evaporated substances a decreased flow rate might be needed to get detectable concentrations.

At dry conditions a sprinkling device 10 can be used for wetting the wheel with a liquid in order to increase the splashing and consequently the sensitivity of the detection. The liquid can be water, ethanol, or mixtures of these, or water and a suitable anti-freezer.

Figure 2:
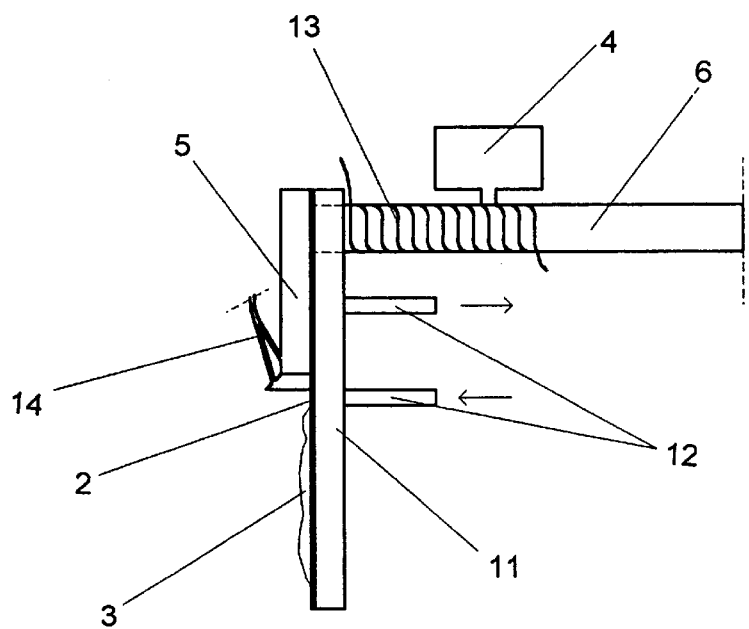
FIG. 2 is a side view of a sampling screen according to the invention.

FIG. 2 shows in detail a view of the sampling screen 2 with auxiliary equipment.

A heating device 11 is heating the sampling screen and the particles 3 deposited on the screen in order to speed up the evaporation of substances. The heating can be done electrically or, as shown in the figure, with a circulating heating medium, i.e. coolant from the engine of the vehicle. The heating device shown consists of a box connected to the back of the sampling screen. The coolant is lead in and lead off through connections 12 and is made to circulate through a channel system in the box. The whole sampling screen 2 and also the air intake 5 is heated by the heating device so that evaporated substances will not condense on cold surfaces.

The air intake 5 is designed to guide the air stream to the conduit 6 in such a way that the air stream will bring substances evaporated from the particles 3 on the contaminated screen. In the embodiment shown the air intake is given the shape of a hood on the upper part of the sampling screen and extends over the complete width of the screen.

The conduit 6 can be provided with a heating device 13, i.e. electrical heating wires, that will heat the conduit at least between the air intake and the detection unit, so that redeposition of evaporated substances and memory effects are avoided.

A cleaning device 14, i.e. in the form of washer jets, can be arranged at the sampling screen 2 for cleaning the screen, when required, from deposited particles. Water, ethanol or mixtures of these, or water and a suitable anti-freezer can be used as a washing fluid.

Many instruments can measure, and in some cases also identify different kinds of chemical compounds when present as vapour in the air and they can be used as detection unit 4 in the invention. Examples of instruments that can be used are AP2C (GIAT) bases on flame photometry, M90 (Environics OY) based on ion mobility, CAM or GID-3 (Graseby Dynamics) based on ion mobility.

The use of the invention is illustrated by the following example:

A distance of 25 meters of a gravelled road was contaminated with tributyl phosphate in an amount of 5 to 10 $g/m^2$. Tributyl phosphate is a compound with a comparable volatility to that of the nerve gas VX. A device according to FIG. 1 with a heated sampling screen and an APC2 as a detection unit was used. Directly after the dispersion, the vehicle was driven on the road in question with a speed of 50 km/h, which immediately gave an indication. At repeated traverses after a few hours the detection became uncertain. Dry conditions were prevailing. After the sprinkling device 10 of the vehicle had been started positive detections could be made during several days after the dispersion.

What is claimed is:

1. Method of detecting chemical contaminants on the ground, characterised in that a tracked or wheeled vehicle (1) having a sampling screen (2) arranged as a mudflap in connection with at least one track/wheel of the vehicle is driven on the ground to be investigated, whereby said sampling screen is contaminated by particles (3) thrown up from the ground and that an air stream carrying substances evaporated from said particles is caused to flow from said sampling screen through a conduit (6) via a detection unit (4) carried by the vehicle.

2. The method as claimed in claim 1, characterised in that the sampling screen (2) is heated by a heating device (11).

3. The method as claimed in claim 1, characterised in that said track/wheel of the vehicle is wetted by a sprinkling device (10).

4. The method as claimed in claim 1, characterised in that the sampling screen (2) is cleaned, when required, by a cleaning device (14).

5. The apparatus for detecting chemical contaminants on the ground, comprising a tracked or wheeled vehicle adapted to be driven on the ground to be investigated, characterised by a sampling screen (2) mounted as a mudflap in connection with at least one track/wheel of the vehicle and being adapted to be contaminated with particles thrown up from the ground surface, and means (5,6,7) for conducting an air stream carrying substances evaporated from said particles, from said sampling screen (2) via a detecting unit (4) carried by in the vehicle.

6. The apparatus for detecting as claimed in claim 5, characterised by a heating device (11) for heating the sampling screen (2).

7. The apparatus for detecting as claimed in claim 5, characterised by a sprinkling device (10) for wetting the track/wheel of the vehicle.

8. The apparatus for detecting as claimed in claim 5, characterised by a cleaning device (14) for cleaning the sampling screen.

9. The apparatus for detecting as claimed in claim 5, characterised in that said means for conducting an air stream from the sampling screen comprises an air intake (5) arranged to gather a flow of air from the contaminated surface of the sampling screen, and a conduit (6) extending from said air intake into the vehicle, via said detection unit (4) and ending on the outside of the vehicle.

10. The apparatus for detecting as claimed in claim 9, characterised in that said conducting means further comprises a fan or an air pump (7) arranged in the conduit (6).

11. The apparatus for detecting as claimed in claim 10, characterised by a throttle-valve (8) arranged in the conduit (6).

12. The apparatus for detecting as claimed in claim 9, characterised in that said conduit (6) being provided with a heating device (13) for heating the conduit (6) between the air intake (5) and the detection unit (4).

* * * * *